(12) United States Patent
Bischoff et al.

(10) Patent No.: US 8,025,659 B2
(45) Date of Patent: Sep. 27, 2011

(54) LASER DEVICE AND METHOD FOR MACHINING MATERIAL USING LASER RADIATION

(75) Inventors: Mark Bischoff, Elleben OT Riechheim (DE); Dirk Mühlhoff, Kunitz (DE); Mario Gerlach, Altenberga (DE)

(73) Assignee: Carl Zeiss Meditec AG, Jena (DE)

( * ) Notice: Subject to any disclaimer, the term of this patent is extended or adjusted under 35 U.S.C. 154(b) by 511 days.

(21) Appl. No.: 10/583,177

(22) PCT Filed: Dec. 15, 2004

(86) PCT No.: PCT/EP2004/014309
§ 371 (c)(1),
(2), (4) Date: May 29, 2007

(87) PCT Pub. No.: WO2005/058216
PCT Pub. Date: Jun. 30, 2005

(65) Prior Publication Data
US 2008/0021443 A1     Jan. 24, 2008

(30) Foreign Application Priority Data
Dec. 16, 2003   (DE) .................. 103 58 927

(51) Int. Cl.
*A61F 9/01* (2006.01)
(52) U.S. Cl. .................. 606/5; 606/2; 128/898
(58) Field of Classification Search .......... 606/2, 4, 606/1, 10, 11, 5, 12; 219/121.6–121.75, 219/121.78–121.86; 372/25–27, 29.01, 29.14; 359/196–198, 201, 203, 216, 220, 227, 228, 359/235, 237, 238, 240, 245, 251–258, 264, 265, 276, 279
See application file for complete search history.

(56) References Cited

U.S. PATENT DOCUMENTS

| | | | |
|---|---|---|---|
| 4,702,245 A | 10/1987 | Schröder et al. |
| 5,350,374 A | 9/1994 | Smith |
| 5,651,784 A | 7/1997 | Klopotek |
| 5,892,569 A | 4/1999 | Van de Velde |

(Continued)

FOREIGN PATENT DOCUMENTS

DE    197 10 597 C1    7/1998
(Continued)

OTHER PUBLICATIONS

Heisterkamp et al., "Optimierung der Laserparameter für die intrastromale Schittführung mittels ultrakurzer Laserpuls," *Der Ophtalmologe*, vol. 98, pp. 623-628 (2001).

*Primary Examiner* — Henry Johnson, III
*Assistant Examiner* — Jeffrey Lipitz
(74) *Attorney, Agent, or Firm* — Patterson Thuente Christensen Pedersen P.A.

(57) ABSTRACT

Disclosed is a laser device for machining material, comprising a laser beam source which supplies pulsed laser radiation, and a variable deflection unit that introduces said laser radiation into the material at different, selectable points so as to create optical breakthroughs. The inventive laser device further comprises a pulse-selecting apparatus which modifies selected laser pulses of the pulsed laser radiation regarding at least one optical parameter in such a way that no more optical breakthroughs can be created using the modified laser pulses.

14 Claims, 3 Drawing Sheets

U.S. PATENT DOCUMENTS

| | | | |
|---|---|---|---|
| 5,933,274 A * | 8/1999 | DeSimone | 359/390 |
| 5,984,916 A | 11/1999 | Lai | |
| 6,096,028 A * | 8/2000 | Bahmanyar et al. | 606/4 |
| 6,110,166 A | 8/2000 | Juhasz | |
| 6,210,401 B1 * | 4/2001 | Lai | 606/12 |
| 6,285,002 B1 | 9/2001 | Ngoi et al. | |
| 6,325,792 B1 * | 12/2001 | Swinger et al. | 606/4 |
| 6,478,792 B1 | 11/2002 | Hänsel | |
| 6,787,733 B2 | 9/2004 | Lubatschowski et al. | |
| 2001/0007496 A1 * | 7/2001 | Modlin et al. | 356/73 |
| 2001/0034025 A1 * | 10/2001 | Modlin et al. | 435/6 |
| 2002/0021730 A1 | 2/2002 | Schroeder et al. | |
| 2003/0127609 A1 * | 7/2003 | El-Hage et al. | 250/574 |
| 2003/0156615 A1 | 8/2003 | Kennedy et al. | |
| 2005/0085800 A1 | 4/2005 | Lenzner et al. | |
| 2005/0107773 A1 | 5/2005 | Bergt et al. | |
| 2006/0268231 A1 * | 11/2006 | Gil et al. | 351/221 |

FOREIGN PATENT DOCUMENTS

| | | |
|---|---|---|
| DE | 199 20 813 A1 | 6/2001 |
| EP | 1 110 661 A2 | 6/2001 |

* cited by examiner

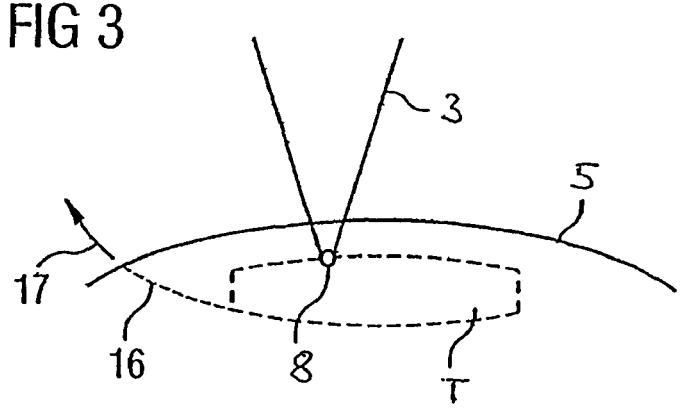
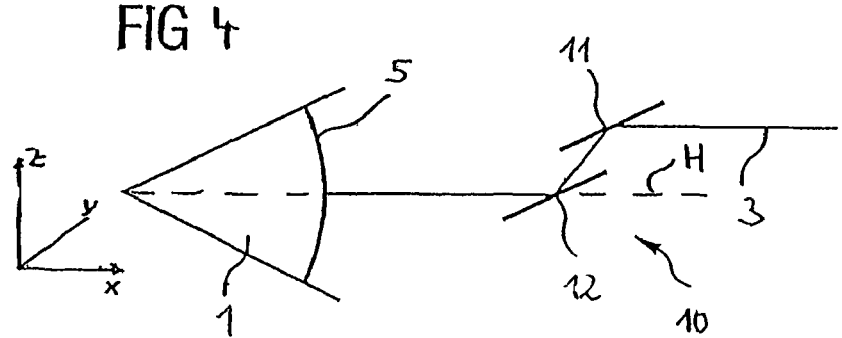
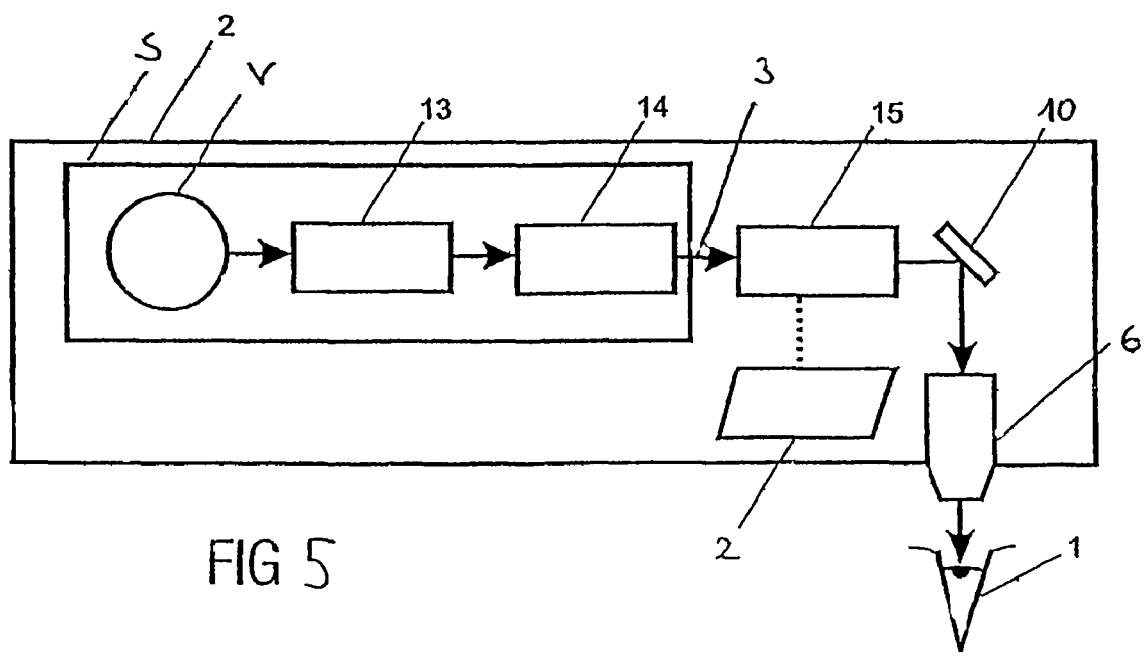

LASER DEVICE AND METHOD FOR MACHINING MATERIAL USING LASER RADIATION

FIELD OF THE INVENTION

The invention relates to a laser apparatus for material treatment, which comprises a source of laser radiation providing pulsed laser radiation and a variable deflecting device, which directs said laser radiation into the material at different, selectable locations, in order to generate optical breakthroughs. The invention further relates to a method of material treatment by means of laser radiation, wherein pulsed laser radiation is generated and deflected into the material in a variable manner so as to generate optical breakthroughs.

BACKGROUND OF THE INVENTION

This laser apparatus, as well as the method of material treatment on which it is based, are particularly useful in forming curved cuts within a transparent material. Curved cuts within a transparent material are generated, for example, in laser-surgical methods, in particular in eye surgery. This involves focusing the treatment laser radiation within the tissue, i.e. beneath the tissue surface, so as to form optical breakthroughs in the tissue.

In the tissue, several processes initiated by the treatment laser radiation then occur in a time sequence. If the power density of the radiation exceeds a threshold value, an optical breakthrough will result, generating a plasma bubble in the material. After the optical breakthrough has formed, said plasma bubble grows due to expanding gases. Subsequently, the gas generated in the plasma bubble is absorbed by the surrounding material, and the bubble disappears again. However, this process takes very much longer than the forming of the bubble itself. If a plasma is generated at a material boundary, which may quite well be located within a material structure as well, material will be removed from said boundary. This is then referred to as photo ablation. In connection with a plasma bubble which separates material layers that were previously connected, one usually speaks of photo disruption. For the sake of simplicity, all such processes are summarized here by the term optical breakthrough, i.e. said term includes not only the actual optical breakthrough, but also the effects resulting therefrom in the material.

For a high accuracy of a laser surgery method, it is indispensable to guarantee high localization of the effect of the laser beams and to avoid collateral damage to adjacent tissue as far as possible. It is, therefore, common in the prior art to apply the laser radiation in a pulsed form, so that the threshold value for the power density of the laser radiation required to cause an optical breakthrough is exceeded only during the individual pulses. In this regard, U.S. Pat. No. 5,984,916 clearly shows that the spatial extension of the optical breakthrough (in this case, of the generated interaction) strongly depends on the pulse duration. Therefore, high focusing of the laser beam in combination with very short pulses allows placement of the optical breakthrough in a material with great point accuracy.

The use of pulsed laser radiation has recently become established practice particularly for laser-surgical correction of visual deficiencies in ophthalmology. Visual deficiencies of the eye often result from the fact that the refractive properties of the cornea and of the lens do not cause optimal focusing on the retina.

U.S. Pat. No. 5,984,916 mentioned above, as well as U.S. Pat. No. 6,110,166, describe methods of producing cuts by means of suitable generation of optical breakthroughs, so that, ultimately, the refractive properties of the cornea are selectively influenced. A multitude of optical breakthroughs are joined such that a lens-shaped partial volume is isolated within the cornea of the eye. The lens-shaped partial volume which is separated from the remaining corneal tissue is then removed from the cornea through a laterally opening cut. The shape of the partial volume is selected such that, after removal, the shape and, thus, the refractive properties of the cornea are changed so as to have the desired correction of the visual deficiency. The cuts required here are curved, which makes a three-dimensional adjustment of the focus necessary. Therefore, a two-dimensional deflection of the laser radiation is combined with simultaneous adjustment of the focus in a third spatial direction. This is summarized herein by the term "deflection".

When forming a cut by joining optical breakthroughs in the material, an optical breakthrough is generated several times faster than the time it takes until a plasma generated therefrom is absorbed by the tissue again. It is known from the publication by A. Heisterkamp, et al., in: Der Ophthalmologe, 2001, 98:623-628, that a plasma bubble grows after an optical breakthrough has been generated in the cornea of the eye at the focal point where the optical breakthrough was generated, which plasma bubble reaches a maximum size after a few ns and then almost completely collapses again. This leaves only small residual bubbles. Said publication states that joining of still growing plasma bubbles will reduce the quality of the cut. Therefore, it suggests a method of the above-mentioned type, wherein individual plasma bubbles are not generated directly next to each other. Instead, a gap is left between two sequentially generated optical breakthroughs, which breakthroughs are generated along a spiral-shaped path. The gap is filled, in a second run, along the spiral with optical breakthroughs and with plasma bubbles resulting therefrom. This is intended to prevent adjacent plasma bubbles from being connected with each other and to improve the quality of the cut.

However, it is generally required to control the distance between two subsequent plasma bubbles along the path line as precisely as possible. In the case of a constant repetition rate, this may be principally effected by adapting the feed speed, i.e. the speed of deflection. In the case of the spiral, this would mean that the laser beam passes along an inner spiral path portion at a much higher speed (i.e. a higher angular frequency) than along an outer path portion. This is a suitable method as long as the maximum frequency of deflection of the scanner system used permits a sufficient feed speed. For the frequency of deflection $f_s$ of the scanner used for lateral deflection of the laser beam, the simple relationship $f_s=(f_L*s)/(2\pi*r)$ holds. In this relationship, $f_L$ is the repetition rate of the pulses in the pulsed laser beam and s is the geometrical distance, measured along the path line, between two plasma bubbles to be generated sequentially along an at least partially circular path line having a radius r. If the maximum frequency of deflection of common galvanometer scanners, which can follow the control signal with good precision up to frequencies of ca. 300 Hz in a non-resonant manner, is assumed for an estimation, this results in a maximum pulse frequency of about 4 kHz for s=10 μm and r=20 μm. With limitations concerning the angles of deflection, even higher pulse frequencies might possibly be put to reasonable use as well. However, this increases positional errors, thus setting practical limits to such procedure. These considerations show that, for presently common scanner systems, it is required to limit the pulse frequency of the laser radiation to a maximum of 10 kHz for generation of desired spiral paths.

As an alternative approach, it would be theoretically conceivable to make the pulse frequency of the laser radiation variable; however, there are certain limitations to such procedure when using laser systems having passively mode-synchronized oscillators. Therefore, for medical applications, the fs laser systems common today only provide laser radiation having a fixed pulse frequency. This leads to technical solutions which have fixed pulse frequencies of the laser radiation in the region of a few kHz. The process speed for generating the cuts is, thus, adapted to those regions of the path which place the highest demands on deflection.

Generating the cuts as quickly as possible is desirable not only for convenience or in order to save time; bearing in mind that movements of the eye inevitably occur during ophthalmological operations, quick generation of cuts also contributes to the optical quality of the result thus achieved and avoids the requirement to track eye movements.

SUMMARY OF THE INVENTION

Therefore, it is an object of the invention to improve a method and an apparatus of the above-mentioned type such that the time required to generate a cut is as short as possible.

According to the invention, the object is achieved by a method of the initially mentioned type, wherein selected laser pulses or picked laser pulses of the pulsed laser radiation are changed, with regard to an optical parameter, such that the changed laser pulses no longer generate optical breakthroughs. The object is further achieved, according to the invention, by a laser apparatus of the initially mentioned type, which comprises a pulse picking device that changes selected laser pulses or picked laser pulses of the pulsed laser radiation, with regard to at least one optical parameter, such that the changed laser pulses no longer allow optical breakthroughs to be generated.

The pulse frequency of the laser radiation which is principally suitable for treatment and is emitted by the final amplification stage of the laser system is, thus, constant and is subsequently changed physically, by means of a suitable apparatus influencing the laser pulses such that only a subset of the generated laser pulses still causes optical breakthroughs in the tissue. Consequently, in contrast to the prior art, the source of laser radiation is no longer optimized, with regard to the repetition rate at which the laser pulses are emitted, to regions of the path line placing the highest demands on deflection (e.g. with the greatest distance between a series of optical breakthroughs), but can now be very much higher. It is possible, for example, to adapt the source of laser radiation in terms of the pulse frequency to the region placing the lowest demands on deflection (e.g. smallest distance, in place or time, between optical breakthroughs which are to be sequentially generated). The picking of the laser pulses allows a stepwise selectable reduction of the repetition rate of the laser pulses, i.e. of the pulse frequency of those pulses which are capable of causing optical breakthroughs, such that limitations of the deflection system are no longer effective. However, this reduction by picking laser pulses does not interfere with the tuning and design of the source of laser radiation, so that the problems mentioned in connection with lasers having a variable pulse frequency do not occur.

The invention enables mutual tuning of the selection of the laser pulses to be changed and of the laser beam deflection such that deflection advantageously occurs as close as possible to the maximum speed of deflection. Thus, a quick generation of cuts is achieved, without having to make any changes to the laser system. For such tuning, it is essential, of course, that the selection of the laser pulses to be changed be selectable.

In particular, a variable distribution of the constant pulse frequency of the laser radiation after leaving the last laser amplifier is possible by means of the apparatus of the invention. Then, ultimately, only every $n^{th}$ laser pulse leaving the laser amplifier will cause an optical breakthrough in the tissue, i.e., for example, every second, or only every third pulse, etc. Of course, said distribution may be made to vary.

For this purpose, a subset of the laser pulses leaving the final laser amplifier at a high pulse frequency is picked and suitably influenced by the pulse picking device of the apparatus according to the invention. Suitably influenced means here that at least one physical parameter of each picked laser pulse is changed such that this pulse can no longer produce an optical breakthrough; in contrast thereto, the other laser pulses (not selected) still cause optical breakthroughs in the focal point. Thus, under the aspect of their effect in the material, the picked laser pulses are "harmless".

A suitable physical parameter which can be influenced according to the invention is, in particular, the phase, the amplitude, the polarization, the beam direction (Poynting vector) or the field distribution over the beam cross-section (beam profile). In particular, these parameters may also be manipulated in the frequency space (in spectral representation), because this is easier to do when changing ultra-short pulses. It is decisive that by influencing the picked laser pulses, a threshold value for the power density in the material which has to be exceeded in order to generate an optical breakthrough is no longer exceeded by the picked pulses. This is achieved indirectly or directly by subsequent interaction of the influenced pulses with an optical system arranged following the source of laser radiation or with certain components of said system.

The pulsed laser radiation is generated with a certain pulse frequency and is then changed with regard to the picked laser pulses, when it has already left the laser system (oscillator and/or amplifier). This avoids adverse effects on the quality, power stability, etc. of the pulsed laser radiation, and dispenses with complicated control of the laser amplifier.

In addition, the procedure according to the invention preferably utilizes the threshold dependence of the non-linear interaction between the treatment radiation and the material in that it is not required to absolutely block out the laser pulses which have been selected and are, thus, not used for treatment, but it already suffices to change the picked laser pulses such that they no longer achieve treatment effects in the material.

The picked laser pulses may be influenced or changed using the most diverse physical principles. What they all have in common is that the optical characteristics of the selected laser pulses can be changed such that they either no longer enter the material to be treated or at least can no longer generate an optical breakthrough therein. In order to effect a change, for example, the principle of acousto-optic modulation, polarization-dependent reflection, fiber-optical switching or periodic absorption, for example by means of a chopper wheel, can be employed.

The laser apparatus for material treatment according to the invention or the method of material treatment by means of laser beams according to the invention generate a cut making better use of the available deflection speed than has been the case in the prior art. A near-maximum utilization is achieved if the deflection speed and the pulse picking are synchronously effected, for example by the action of a corresponding control device. It is then possible to increase the picking, i.e.

to select more pulses which cannot generate optical breakthroughs, if deflection approaches a maximum deflection speed. Due to the increase in picking, fewer pulses capable of generating an optical breakthrough arrive at the deflection device within a given time unit. This allows working at a lower deflection speed. The synchronous control of deflection and picking takes this into account.

BRIEF DESCRIPTION OF THE DRAWING

The invention will be explained in more detail below, by way of example and with reference to the Figures, wherein:

FIG. 3 shows a schematic representation illustrating a cut generated during laser-surgical treatment with the instrument of FIG. 1;

FIG. 4 shows a deflection device of the laser-surgical instrument of FIG. 1;

FIG. 5 shows a block diagram of the instrument of FIG. 1;

DETAILED DESCRIPTION OF THE DRAWINGS

Figure 1:
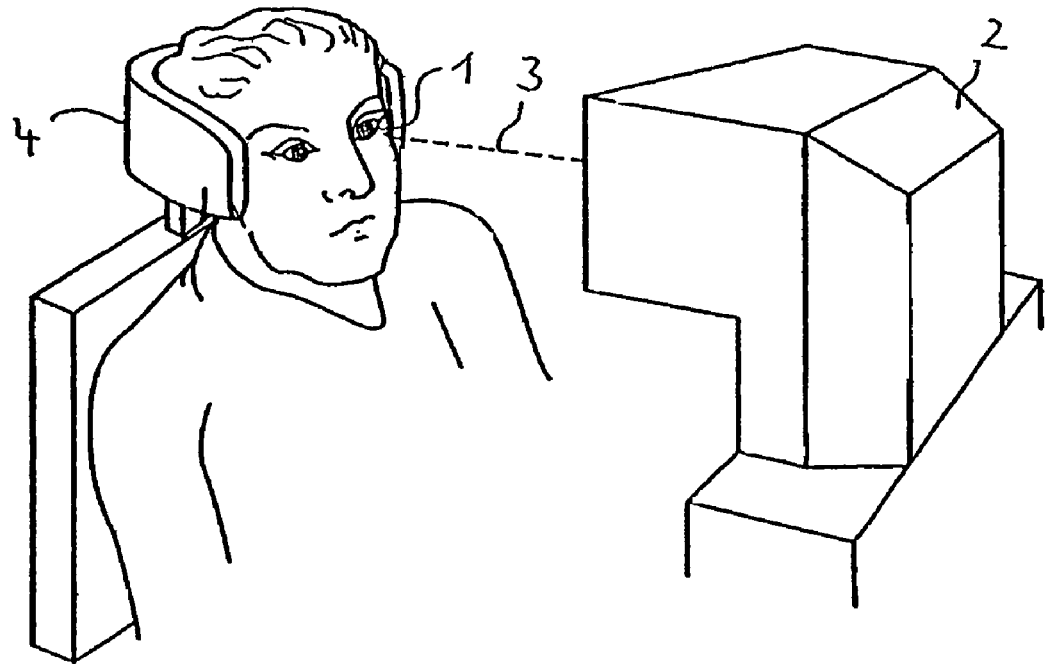
FIG. 1 shows a perspective view of a patient during treatment using a laser-surgical instrument.

FIG. 1 shows a laser-surgical instrument for treatment of an eye 1 of a patient, said laser-surgical instrument 2 serving to effect a refractive correction. For this purpose, the instrument 2 emits a treatment beam 1 onto the eye of the patient 1 whose head is immobilized in a head holder. The laser-surgical instrument 2 is capable of generating a pulsed laser beam 3 allowing the method described in U.S. Pat. No. 6,110,166 to be carried out. The laser beam 3 consists of fs laser pulses having a pulse frequency of between 10 and 500 kHz. In the exemplary embodiment, the components of the instrument 2 are controlled by an integrated control unit.

Figure 2:
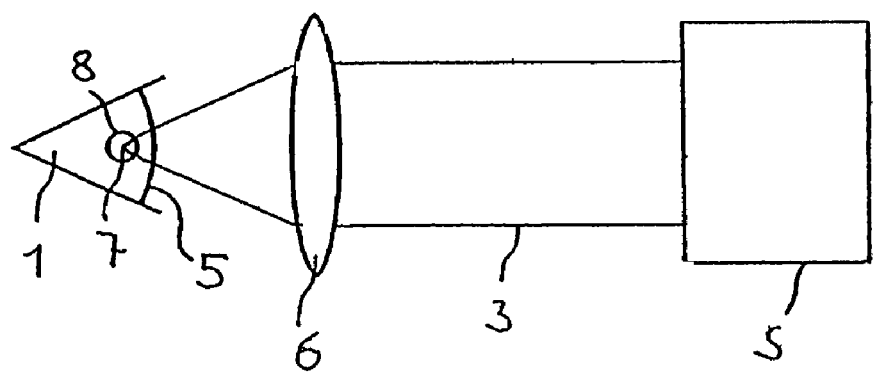
FIG. 2 shows the focusing of a beam onto the eye of the patient with the instrument of FIG. 1.

As schematically shown in FIG. 2, the laser-surgical instrument 2 comprises a source of radiation S whose radiation is focused into the cornea 5 of the eye 1. A visual deficiency in the eye 1 of the patient is remedied using the laser-surgical instrument 2 to remove material from the cornea 5 so as to change the refractive characteristics of the cornea by a desired amount. In doing so, the material is removed from the stroma of the cornea, which is located beneath the epithelium and the Bowman's membrane and above the Decemet's membrane and the endothelium.

Material removal is effected in that layers of tissue are separated by focusing the high-energy pulsed laser beam 3 by means of an adjustable telescope 6 in a focus 7 located in the cornea 5. Pulses of the pulsed laser radiation 3 generate an optical breakthrough in the tissue, said breakthrough in turn initiating a plasma bubble 8. Thus, the separation of tissue layers comprises a larger area than the focus 7 of the laser radiation 3, although the conditions for achieving the breakthrough are achieved only in the focus 7. By suitable deflection of the laser beam 3, many plasma bubbles 8 are now generated during treatment. These plasma bubbles then form a cut 9, which circumscribes a partial volume T of the stroma, namely the material to be removed from the cornea 5.

Due to the laser radiation 3, the laser-surgical instrument 2 operates in the manner of a surgical knife which, without injuring the surface of the cornea 5, separates material layers within the cornea 5. If a cut 16 is effected up to the surface of the cornea by generating further plasma bubbles 8, the material of the cornea 5 isolated by the cut 9 can be pulled out of the cornea 5 laterally in the direction of the arrow 17 and thus removed.

The generation of the cut 9 by means of the laser-surgical instrument 2 is schematically shown in FIG. 3. The cut 9 is formed by a series of plasma bubbles 8 produced as a result of continuous displacement of the focus 7 of the pulsed focused laser beam 3.

On the one hand, the focus displacement according to one embodiment is effected by means of the deflecting unit 10, schematically shown in FIG. 4, which deflects the laser beam 3 along two mutually perpendicular axes, said laser beam 3 being incident on the eye 1 on a main axis of incidence H. For this purpose, the deflecting unit 10 uses a line mirror 11 as well as an image mirror 12, thus resulting in two spatial axes of deflection which are located behind each other. The point where the principal beam axis H and the deflection axis cross (in projection onto one of the axes) is then the corresponding point of deflection. On the other hand, the telescope 6 is suitably adjusted for focus displacement. This allows adjustment of the focus 7 along three orthogonal axes in the x/y/z coordinate system schematically shown in FIG. 4. The deflecting unit 10 adjusts the focus in the x/y plane, with the line mirror allowing adjustment of the focus in the x-direction and the image mirror allowing adjustment of the focus in the y-direction. In contrast thereto, the telescope 6 acts on the z-coordinate of the focus 7. Thus, on the whole, three-dimensional deflection of the focus 7 is achieved.

Due to the corneal curvature, which is between 7 and 10 mm, the partial volume T also has to be curved accordingly. The corneal curvature thus requires an image field curvature. This is effected by suitable control of the deflecting unit 10 and of the telescope 6.

FIG. 5 shows a simplified block circuit diagram of the laser-surgical instrument 2 for refractive surgery on the human eye 1. Only the most important details are shown: an fs laser serving as the source of radiation S, which laser consists of an fs oscillator V, as well as of one or more amplification stages 13, and following which laser, there is also arranged a compressor or pre-compressor 14 in this case; a laser pulse modulator 15 having the laser radiation from the laser S applied thereon; the deflecting unit 10, which is realized as a scanner here; an objective realizing the telescope 6 for focusing into the tissue to be treated, and the control unit 17.

The laser S generates laser pulses each having a duration in the fs range. First, the laser pulses enter the laser pulse modulator 15, which effects a picking (in a manner to be described later) of those laser pulses which shall not generate optical breakthroughs in the tissue. Subsequently, at least the non-selected laser pulses pass to the scanner 10 and through the objective 6 into the patient's eye 1. There, they are focused and generate optical breakthroughs in the focus 7. Although the selected laser pulses may also pass to the scanner 10 and further to the objective 6 and into the eye 1, they differ from the other laser pulses in at least one physical parameter, such that they do not cause an optical breakthrough in the eye 1.

There are various possible positions for the laser pulse modulator 15. It is advantageous, in some cases, to arrange said modulator immediately following the final amplification stage 13, i.e. preceding the compressor/pre-compressor 14. Thus, it may also be incorporated into the constructional space of the laser S, but it will be located following the amplification system and the oscillator. If a cavity-dumped oscillator is used, the laser pulse modulator 15 is always located within the resonator.

Figure 6:
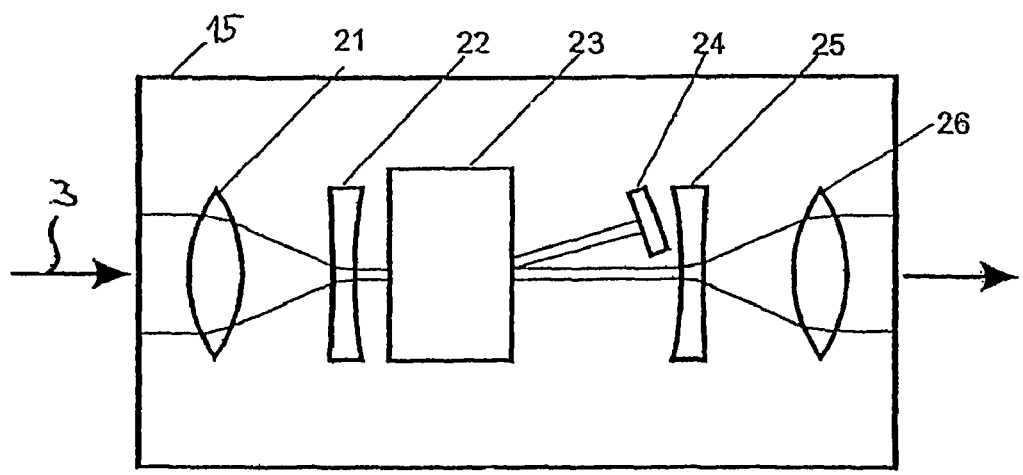
FIG. 6 shows a schematic representation of an embodiment of a laser pulse modulator of the instrument of FIG. 1.

FIG. 6 shows an alternative embodiment of the laser pulse modulator 15. The generated laser beam 3 is first formed by means of lenses 21 and 22 and then guided into an acousto-optic modulator 23 (AOM). The lenses 21 and 22 are examples of optical components which are suitable to form a beam (e.g. mirrors, lenses, DOE).

The AOM 23 is controlled by an electrical control signal from the control unit (not shown here) so as to pick those laser pulses which are not intended to generate optical breakthroughs. In the illustrated case, the process of picking consists in diffraction of the laser pulses in the AOM 23 and in non-diffracted transmission of the other laser pulses.

The diffracted laser pulses are absorbed at a ray trap 24 or are at least no longer capable of causing optical breakthroughs. The ray trap 24 may then be omitted. The effect of an overlap of the change in direction of the picked laser pulses caused by the diffraction with an amplitude modulation of the presently embodied alternative of the laser pulse modulator 15 consists in reducing the pulse peak performance of the selected laser pulses such that they no longer generate an optical breakthrough even after focusing in the eye 1. The other laser pulses remain essentially unchanged and do generate optical breakthroughs in the eye 1.

Of course, an inverted embodiment of the apparatus according to the invention, wherein the selected laser pulses pass through an AOM 23 without being diffracted and wherein the other laser pulses are suitably diffracted, is also possible.

This variant has the advantage that the selected laser pulses which are not intended to generate optical breakthroughs can be removed completely from the treatment laser beam. However, in the diffraction process, the other laser pulses also undergo several changes which might reduce their suitability for material treatment. These changes are essentially related to the high spectral bandwidth of ultra-short laser pulses and can often be compensated for with little effort.

Instead of the described AOM 23, the utilized modulator may be an electro-optic modulator (EOM), a Pockels' cell, a liquid crystal element (LC element), a fiber optics switching element, or a chopper wheel, respectively supplemented with components which cause transformation of the primarily changed optical properties of the picked laser pulses so as to prevent the generation of optical breakthroughs in the focus.

Also, for the purpose of selection, the laser pulse may be lengthened in time (elongation), for example, by dispersion. This effect can be achieved, for example, by polarization rotation of the picked laser pulses by means of a suitable transformation—e.g. using polarization-dependent reflection. Fast polarization rotations can be caused by Pockels' cells.

Wavefront changing of the picked laser pulses which leads to insufficient focusing and, thus, to the absence of optical breakthroughs is certainly possible, too. The laser pulses are then defocused such that the peak power density no longer suffices to initiate optical breakthroughs. Such wavefront changes can be achieved, e.g. by liquid crystal elements or also by membrane mirrors, such as those known from adaptive optics.

Figure 7:
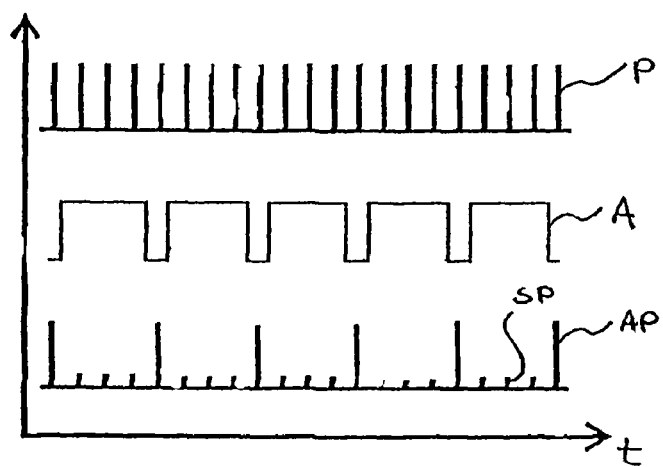
FIG. 7 shows time sequences of laser pulses and electrical control signals for the laser pulse modulator of FIG. 6.

The control unit 18 effects control of the laser pulse picking. A suitable control signal A is indicated, by way of example, in FIG. 7. What is further shown is how the laser pulse intensity of the laser pulses P emitted by the last laser amplifier at a constant pulse frequency is modulated so as to thus effect the desired pulse picking. The picked laser pulses SP with reduced pulse intensity do not cause a plasma in the material and the effective pulse frequency of treating laser pulses AP is thus reduced. In the case of an AOM being used, the control signal A as shown represents the envelope of the high-frequency electrical signal by which the AOM is operated.

The described concept is advantageously usable in laser material treatment, particularly in micro-treatment of materials using spectrally broadband laser pulses. Utilizing spectrally broadband laser pulses obtains an effect in the material in many cases due to a high photon density causing a non-linear interaction of the material with the treatment radiation, which in turn causes a desired change in the material. This non-linear interaction is particularly easy to prevent, because it exhibits a strong threshold value characteristic, i.e. it is initiated only above a radiation power density threshold value.

Changing the beam parameters allows precise selection for each pulse as to whether it has a treatment effect or not. The proposed apparatus is usable also in the treatment of non-organic materials, e.g. in the manufacture of wave guide structures in transparent materials. Advantageously, a use in connection with the manufacture of micro-mechanical components may also be effected, too.

The invention claimed is:

1. A laser apparatus for material treatment, comprising:
a source of laser radiation providing pulsed laser radiation comprising a train of laser pulses; and
a deflecting device, which directs said laser radiation into the material at different, selectable locations to generate optical breakthroughs within the material; and
a pulse picking device that modifies selected laser pulses of the train of laser pulses, with regard to at least one optical parameter of said selected laser pulses, such that the selected laser pulses cannot generate optical breakthroughs; and
a control device operably coupled to the source of laser radiation, the deflecting device and the pulse picking device, and the control device being operable to monitor and control the source of laser radiation, the deflecting device and the pulse picking device;
the control device being further operable to control the operation of the pulse picking device such that the pulse picking device influences said selected laser pulses such that only a remaining subset of not selected laser pulses cause optical breakthroughs within the material and such that a number of selected pulses varies in relation to a deflection speed of the deflecting device.

2. The laser apparatus as claimed in claim 1, wherein the laser pulses of the train of laser pulses are substantially equidistant in time and wherein the control device is programmed to operate the pulse picking device such that the pulse picking device selects non-consecutive laser pulses of the train of laser pulses, the selected laser pulses being substantially equidistant in time according to a selection frequency.

3. The laser apparatus as claimed in claim 2, wherein the control device controls the pulse picking device and the deflecting device to generate the optical breakthroughs along a predetermined path.

4. The laser apparatus as claimed in claim 3, wherein the control device monitors an actual deflection speed of the deflecting device and if the actual deflection speed of the deflecting device approaches a preselected maximum deflection speed, the control device increases the selection frequency of pulses such that more pulses are selected and also decreases the actual deflection speed.

5. The laser apparatus as claimed in claim 1, wherein the control device is programmed to operate the pulse picking device such that the pulse picking device modifies the selected laser pulses at least with regard to one parameter selected from a group consisting of: phase, amplitude, polarization, propagation direction, and beam profile.

6. The laser apparatus as claimed in claim 1, wherein the pulse picking device comprises at least one structure selected from a group consisting of an acousto-optic modulator, a Pockels' cell, a fiber-optics switching element and a chopper wheel.

7. The laser apparatus as claimed in claim 1, wherein the control device synchronously controls the pulse picking device and the deflecting device.

8. A method of material treatment by laser radiation, comprising
generating pulsed laser radiation comprising a train of laser pulses via a laser source controlled by a control unit;
variably deflecting the pulsed laser radiation into the material to generate optical breakthroughs within the material with a deflecting device that is controlled by the control unit;
selecting a subset of selected laser pulses with a pulse picking device controlled by the control unit; and
modifying the selected laser pulses of the train of laser pulses, with regard to an optical parameter of said selected laser pulses, such that the selected laser pulses no longer generate optical breakthroughs, wherein only a remaining subset of not selected laser pulses cause optical breakthroughs within the material and such that a number of selected pulses varies in relation to a deflection speed of the deflecting device.

9. The method as claimed in claim 8, wherein the laser pulses of the train of laser pulses are substantially equidistance in time and the method further comprising:
selecting non-consecutive laser pulses of the train of laser pulses according to a selection frequency, the selected laser pulses being substantially equidistant in time.

10. The method as claimed in claim 9, further comprising deflecting the laser radiation and the change in the selected laser pulses in a synchronized manner.

11. The method as claimed in claim 9, further comprising, if an actual deflection speed of said deflection comes close to a maximum deflection speed, increasing the selection frequency of pulses such that more pulses are selected, and simultaneously decreasing the actual deflection speed.

12. The method as claimed in claim 8, wherein the selected laser pulses are modified at least with regard to one parameter selected from a group consisting of: phase, amplitude, polarization, propagation direction, and beam profile.

13. The method as claimed in claim 8, further comprising controlling the deflection of the laser radiation and the selection of the laser pulses to cause optical breakthroughs to form along a predetermined path within the material.

14. The method as claimed in claim 13, further comprising, if an actual deflection speed of said deflection comes close to a maximum deflection speed, increasing the selection frequency of pulses such that more pulses are selected, and simultaneously decreasing the actual deflection speed.

* * * * *